US006786427B2

(12) United States Patent
Schram et al.

(10) Patent No.: US 6,786,427 B2
(45) Date of Patent: Sep. 7, 2004

(54) LIQUID SEALING ARRANGEMENTS FOR REPLACEABLE LIQUID RESERVOIRS

(75) Inventors: David J. Schram, Waterford, WI (US); Stephen M. Doerr, Racine, WI (US); Maryann Jashinske, Acworth, GA (US); John A. Boticki, Racine, WI (US); James L. Bournoville, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 10/323,006

(22) Filed: Dec. 19, 2002

(65) Prior Publication Data

US 2004/0118936 A1 Jun. 24, 2004

(51) Int. Cl.[7] ......................... A01G 27/00; A24F 25/00; A61L 9/04; B65D 23/12; B67D 3/00

(52) U.S. Cl. ......................... 239/145; 239/44; 215/386; 220/694; 222/187

(58) Field of Search ............................ 239/145, 44, 34, 239/50, 326, 45–47, 600; 222/187, 570; 248/309.1, 311.2, 312; 220/694; 215/227, 386, 228

(56) References Cited

U.S. PATENT DOCUMENTS

| | | | | |
|---|---|---|---|---|
| 5,364,027 A | * | 11/1994 | Kuhn | 239/44 |
| 5,909,845 A | * | 6/1999 | Greatbatch et al. | 239/44 |
| 6,354,513 B1 | * | 3/2002 | Basaganas Millan | 239/44 |

* cited by examiner

*Primary Examiner*—Michael Mar
*Assistant Examiner*—Darren Gorman
(74) *Attorney, Agent, or Firm*—Fitzpatrick, Cella, Harper & Scinto

(57) ABSTRACT

A plug and wickholder is configured to be reliably sealed to the neck of a bottle which contains a liquid to be atomized and to a cap which seals the bottle during storage. The plug and wickholder includes a first generally tubular wall which contains a wick and which fits tightly into a cap sealing wall, and it further includes a generally cylindrical sealing wall which fits tightly into a bottle neck. A second generally vertical tubular wall is interposed between the first generally tubular wall and the generally cylindrical sealing wall.

22 Claims, 4 Drawing Sheets

LIQUID SEALING ARRANGEMENTS FOR REPLACEABLE LIQUID RESERVOIRS

BACKGROUND OF THE INVENTION

1. Field of the Invention

This invention relates to replaceable liquid reservoirs which contain liquids to be dispersed in atomizer devices; and more particularly it concerns novel sealing arrangements for such replacement reservoirs which reliably protect against leakage of liquid during transportation, storage and use.

2. Description of the Related Art

Replacement reservoirs which contain liquids to be dispersed in an atomizing device are known. These reservoirs generally comprise a bottle for containing the liquid, and a plug and wickholder which seals across the neck of the bottle. A wick extends from the liquid within the bottle and up through the plug and wickholder to deliver the liquid to the atomizing device.

It is important to provide a reliable and durable liquid seal between the bottle and the plug and wickholder during both storage and use and to provide a reliable and durable seal between the plug and wickholder and a removable sealing cap which covers the upper end of the wick during storage of the replaceable reservoir. Because many liquids which are dispersed in atomizer devices, such as fragrances and insecticides, have very low viscosity and are highly volatile, a generally tight interference fit is required between the mating parts of the reservoir in order to achieve reliable sealing. However the forces involved in forming an interference fit between the bottle and plug and wickholder should not interfere with the forces involved in forming an interference fit between the plug and wickholder and an overcap which seals around the wick during storage. That is, the forces involved in forming one seal should not cause stresses which affect the integrity of the other seal.

U.S. Pat. No. 6,293,474 describes an atomizing device in which liquid contained in a liquid container is drawn up through an open neck of the container by means of a wick to a vibrating orifice plate. A combination plug and wickholder closes the open neck of the container. This plug and wickholder is a unitary molded member which includes an inner vertical tubular wall for containing and supporting the wick, a radially extending horizontal wall which extends outwardly from the tubular wall, and an outer peripheral skirt which extends downwardly from the outer edge of the horizontal wall and clamps over a bead on the outer surface of the neck of the container. A tubular sealing wall projects downwardly from the undersurface of the horizontal wall and fits tightly inside and seals the neck of the container to seal the plug to the container.

U.S. Pat. Nos. 6,296,196, 6,341,732, 6,386,462, 6,382,522, 6,446,880 and 6,450,419 and assigned to the assignee of this application, describe an improvement to the earlier plug and wickholder wherein the horizontal wall portion between the tubular sealing wall and the wickholder is moved down to the lower portion of these elements so that they are connected to each other at the their lower edges. This exposes a large surface area on the outer surface of the tubular wickholder over which a tubular cap can fit to tightly to seal the wick from the atmosphere.

SUMMARY OF THE INVENTION

The present invention provides improvements which isolate the stresses which occur when a cap is mounted on and sealed to the plug and wickholder from the stresses which occur when the plug and wickholder are mounted on and sealed to the liquid container or reservoir. By virtue of this isolation, it becomes possible to provide high sealing forces for each seal, i.e. the seal between the cap and the plug and wickholder and the seal between the plug and wickholder and the liquid reservoir or bottle, without causing undue stresses which could cause cracking and leakage during assembly, shipping and storage.

The invention in one aspect involves a combination plug and wickholder comprising a unitary molded plastic piece. This plastic piece includes first and second generally vertical tubular walls, a generally horizontal upper wall, a circumferential skirt extending down from the upper wall and a generally cylindrical sealing wall extending down from the upper wall to press and seal against the inner surface of the neck of a liquid container. The first tubular wall contains and supports a wick extending up from within the container. The second tubular wall extends around and is concentric with the first wall. The first and second tubular walls are connected to each other near their lower ends. The horizontal upper wall, which is configured to be fitted over the top of a container or bottle neck, is integral with and extends radially outwardly from the second tubular wall near its upper end. The circumferential skirt extends down from the outer edge of the radially extending upper wall. The skirt is formed on its internal surface near the bottom edge thereof with latch elements to hold the skirt to the neck of a container or bottle. The generally cylindrical sealing wall extends down from the upper wall between the skirt and the second tubular wall for fitting inside of and becoming sealed to the inside surface of the container or bottle neck when the latch elements hold the skirt to the container or bottle neck. The cylindrical wall is free of other structure at its lower edge. By virtue of this configuration, the stresses caused by sealing a cap to the tubular wickholder and the stresses caused by sealing the cylindrical wall to the inner surface of the container or bottle are isolated from each other so that sealing of the one does not cause a danger of creating a leakage condition from the other. At the same time the stresses involved in attaching the plug and wickholder to the container or bottle are isolated so that the danger of cracking and consequent leakage is avoided.

The invention in another aspect involves a subassembly comprising a plug and wickholder as above described in combination with a removable sealing overcap. In a still further aspect the invention involves a subassembly comprising a plug and wickholder as above described mounted on a bottle such that a liquid to be dispersed is transferred from the bottle via a wick which extends through the plug and wickholder. In yet another aspect the invention involves a combination comprising a plug and wickholder, as above described, mounted on a bottle and a sealing overcap which encloses a wick extending from within the bottle and out through the plug and wickholder.

DETAILED DESCRIPTION OF THE PREFERRED EMBODIMENT

Figure 1:
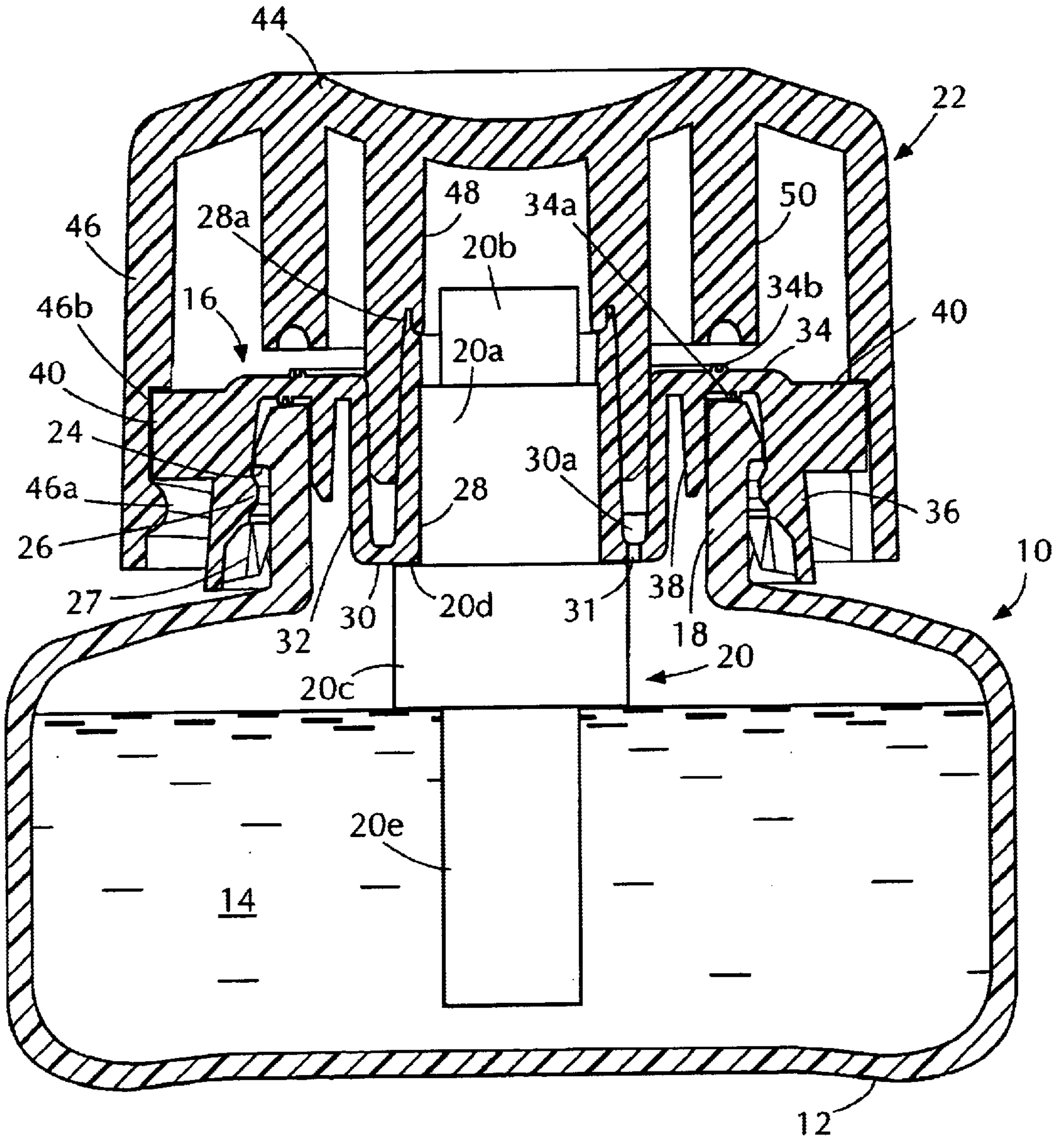
FIG. 1 is a cross section, taken in elevation, of a replaceable reservoir or bottle which contains a liquid to be atomized and which has been capped for storage, according to the invention.

As shown in FIG. 1 a replaceable reservoir 10 comprises a bottle 12 which contains a liquid 14 to be atomized. A plug and wickholder 16 is securely fitted to a neck 18 of the bottle 12 in a manner to form a first liquid tight seal with the neck. A wick 20 extends up from the liquid 14 within the bottle and out through the plug and wickholder 16. A removable sealing cap 22 covers the plug and wickholder in a manner to form a second liquid tight seal around the upper end of the wick 20.

The bottle 12 is preferably molded from a hard plastic material which provides a good gas barrier and which can be formed by injection blow molding, extrusion blow molding or a similar process. A suitable material is an impact modified acrylonitrile-methyl acrylate copolymer such as Barex® 210 injection grade resin. Other materials that could be used include glass and polyproplyene. An outer retaining shoulder 24 is formed around the upper region of the bottle neck 18. This shoulder interacts with a bead 26 on the plug and wickholder 16 to secure the plug and wickholder to the bottle 12. Anti-rotation grooves 27 are formed just below the bead 26 to prevent the plug and wickholder 16 from rotating relative to the bottle after assembly.

The plug and wickholder 16 is molded as an integral unitary piece from a suitable plastic such as polypropylene. The plug and wickholder 16 includes a vertical inner tubular wall 28 for holding the wick 20 in vertical orientation in the center of the bottle neck 18. A circumferential lip 28*a* is formed about the upper end of the wall 28. A lower radial wall 30 extends out from the lower edge of the inner tubular wall 28. A vertical outer tubular wall 32 extends upwardly from the outer edge of the radial wall 30 and surrounds the inner tubular wall 28. A vent and hole 31 is formed in the lower radial wall 30 to provide venting as the liquid 14 is removed from the bottle 12 via the wick 20. A pair of vertical walls 30*a* extend up from the wall 30 on each side of the vent hole 31 to prevent it from becoming plugged with liquid. A horizontal upper wall 34 extends outwardly from the upper end of the outer tubular wall 32 and extends, at its outer edge, over the rim of the bottle neck 18. Circumferential crush ribs 34*a* are formed on the under side of the upper wall 34 to provide cushioning when the plug and wickholder 16 is forced down onto the bottle neck 18.

A peripheral skirt 36 extends downwardly from the outer edge of the upper wall 34. A bead 26 is formed around the inner surface of the peripheral skirt 36 to interact with the shoulder 24 on the bottle neck 18 to hold the plug and wickholder securely on the bottle 12. The bead 26 is preferably formed in circumferential segments to reduce stress in assembling the plug and wickholder 16 to the bottle 12. The amount of interference between the bead 26 of the plug and wickholder 16 and the shoulder on the bottle neck 18 is designed to maintain the plug and wickholder firmly locked onto the bottle and to maintain a reliable seal between these plug and wickholder and the bottle.

A cylindrical sealing wall 38 extends downwardly from the under side of the upper wall 34 to project into the bottle neck 18. The sealing wall 38 is dimensioned, preferably by means of a slight taper, to form an interference fit with the inner surface of the bottle neck when the plug and wickholder 16 is assembled with bottle 12. This interference fit provides an excellent seal between the bottle 12 and the plug and wickholder 16 because it develops high sealing forces between the mating surfaces of the sealing wall 38 and the bottle neck 18. It is important, however, that the sealing wall 38 not be subjected to stresses or distortion from the flexing of other portions of the plug and wickholder 16. To achieve this end, the lower end of the cylindrical sealing wall 38 is configured to be free of any other structural attachment.

A pair of bayonet mounting lugs 40 extend radially outward from the outer edge of the upper wall 34. These mounting lugs fit into a bayonet joint in an atomizing device (not shown) for holding the bottle and wick in the device.

The wick 20 may be made of a material having capillary passages extending from its lower end to its upper end. However, it will be appreciated that the particular composition or construction of the wick 20 is not critical to this invention. The wick 20 extends up into and through the inner tubular wickholder wall 28. The wick is formed with a central portion 20*a* having a diameter which fits closely in and terminates inside the wickholder wall 28. A smaller diameter upper portion 20*b* extends up from the central portion 20*a* to a location just above the wickholder wall 28. An enlarged diameter portion 20*c* extends down from the central portion 20*a* and forms a shoulder 20*d* under the lower radial wall 30 of the plug and wickholder to limit upward movement of the wick 20. A lower, smaller diameter portion 20*e* extends down form the enlarged diameter portion 20*c* and into the liquid 14 in the bottle 12 as shown.

As shown in FIG. 1, the removable sealing cap 22, which is also preferably molded of a suitable plastic material such as polypropylene, comprises a generally circular top wall 44 which extends over the plug and wickholder 16. A peripheral skirt 46 extends downwardly from the outer edge of the top wall 44 and over the bayonet mounting lugs 40 on the plug and wickholder 16. As can be seen, the skirt 46 is formed with an internal thread 46*a* which extends in a spiral manner under the bayonet lugs to hold the cap onto the plug and wickholder 16.

Figure 2:
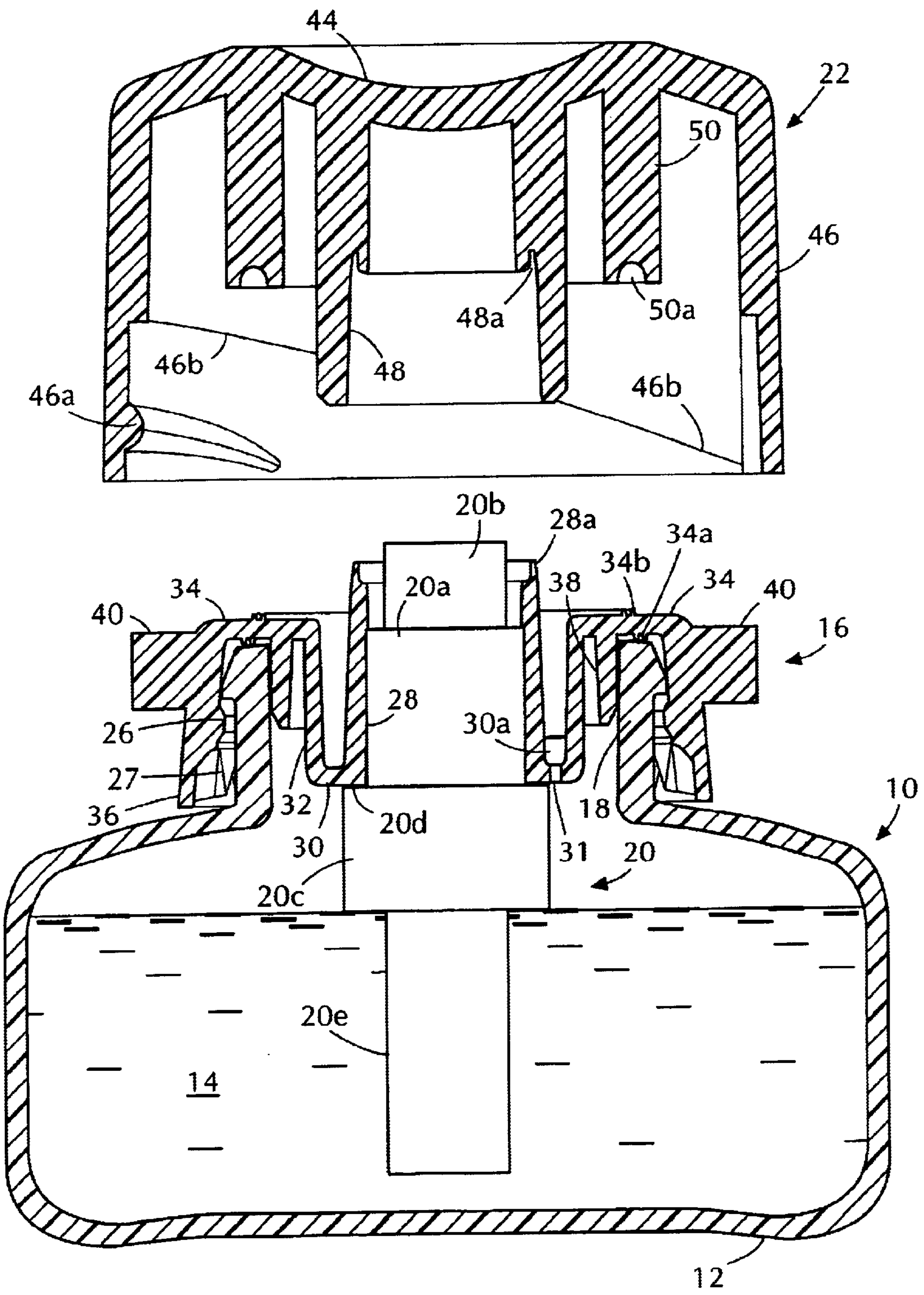
FIG. 2 is a view similar to FIG. 1 but showing the cap removed from the replaceable reservoir before installing it in an atomizing device.

The cap skirt 46 is also formed with internal shoulders 46*b* which are spaced from and extend parallel to the internal thread 46*a*. The shoulders 46*b* fit over the bayonet mounting lugs 40. As shown in FIG. 2, the shoulders 46*b* spiral downwardly inside the skirt 46. This construction allows the cap 22 to be easily removed from the plug and wickholder prior to mounting the bottle in an atomizer device. The cap is removed simply by turning it so that its shoulders 46*b* ride up on the mounting lugs 40 of the plug and wickholder 16. This lifts the cap 22 off from the plug and wickholder so that the bottle 12 with the plug and wickholder 10 mounted thereon can be fitted to an atomizer device.

The cap 22 is also formed with a tubular inner sealing wall 48 which extends down from its top wall 44. The inner sealing wall 48 extends over the top of the wick 20 and fits tightly around the outer surface of the inner tubular wall 28 of the plug and wickholder 16, thus forming a liquid tight enclosure for the wick 20 while the cap 22 is mounted on the plug and wickholder. The inner and outer surfaces of the sealing wall 48 and the mutually facing surfaces of the inner tubular wall 28 and the outer tubular wall 32 are configured to form an interference fit, for example by shaping at least one of each pair of mating surfaces with a slight taper. This ensures that liquid which is drawn up through the wick 20 will not leak out from the bottle 12 during storage when the cap 22 is in place; and it also seals the vent hole 31 from leakage. The inner region of the sealing wall 48 is also formed with a recess 48*a* which accommodates the lip 28*a* of the inner wall 28 of the plug and wickholder 16 to enhance sealing.

The cap 22 is also formed with a tubular abutment wall 50 which surrounds the sealing wall 48. The abutment wall 50 has a relatively large thickness in order to enable it to transmit vertical forces encountered during assembly of the bottle 12 with the subassembly comprising the cap 22 and the plug and wickholder. The abutment wall, as shown, rests upon the upper surface of the upper wall 34 of the plug and wickholder 16 at a location above the upper edge of the bottle neck 18. Also, as can be seen, the end of the abutment wall has a round recess 50*a* which accommodates the sealing ribs 34*b* so that downward forces on the cap 22 are not imposed on these sealing ribs.

Figure 3:
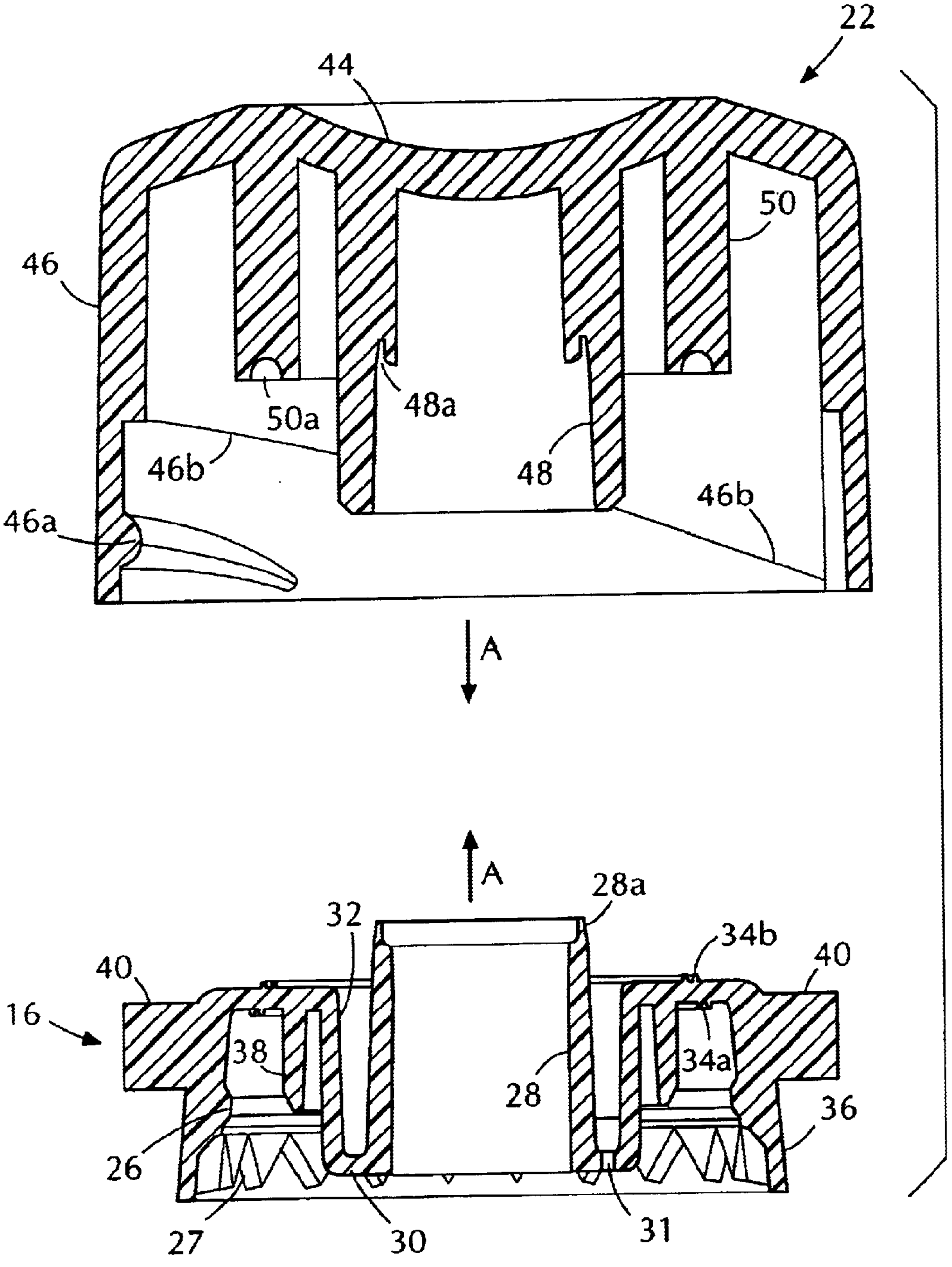
FIG. 3 is a cross section taken in elevation, of a cap and a wickholder prior to being joined together to form a closure subassembly which, after the insertion of a wick, becomes secured to a liquid container or bottle.

In assembling a replaceable reservoir, the plug and wickholder 16 is first connected to the cap 22 to form a subassembly by bringing the cap and the plug and wickholder together as indicated by the arrows A in FIG. 3. The cap then becomes affixed to the plug and wickholder 16 by twisting the cap so that the mounting lugs 40 of the plug and wickholder 16 become screwed into the spiral space between the thread 46*a* and the shoulders 46*b* formed inside the cap skirt 46. During this assembly, the tubular sealing wall 48 of the cap 22 becomes forced into the space between the inner and outer tubular walls 28 and 32 of the plug and wickholder 16. As mentioned above, the mating surfaces of these walls form an interference fit which ensures a reliable liquid seal between them.

Figure 4:
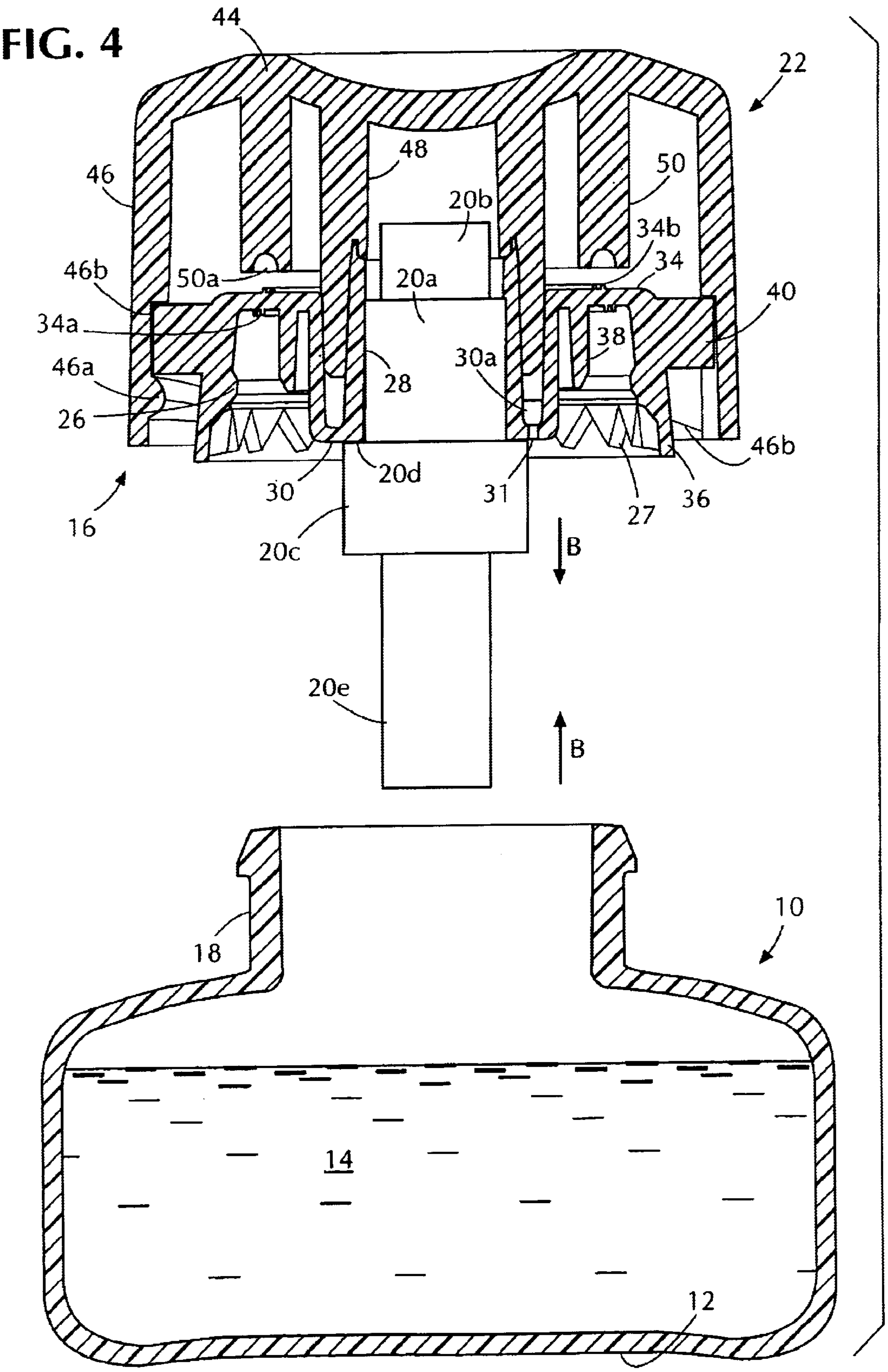
FIG. 4 is a view similar to FIG. 3 but showing the closure subassembly and a liquid container or bottle prior to their being joined together.

The next step in assembling the reservoir, as seen in FIG. 4, is to insert the wick 20 into the inner tubular wall of the plug and wickholder 16. Then, as shown in FIG. 4, the bottle 12, filled with liquid 14 to be atomized; and the subassembly formed by the plug and wickholder 16, the wick 20 and the cap 22, are brought together as indicated by the arrows B in FIG. 4. Force is applied against the bottle 12 and the cap 22 to snap the bead 26 on the plug and wickholder over the shoulder 24 on the bottle neck 18. At the same time the sealing wall 38 on the plug and wickholder 16 is forced into the bottle neck 18 to form a liquid tight seal between them.

In order to achieve a tight seal between the plug and wickholder 16 and the bottle 12 and to connect these member in a manner which ensures that they cannot easily be separated, the shoulder 24 on the bottle neck 18 and the bead 26 on the skirt 36 of the plug and wickholder 16 should be designed with sufficient interference to provide a seal. In order avoid damage to the subassembly comprising the cap 22, the wick 20 and the plug and wickholder 16, the large force needed to overcome this interference is applied to the cap top wall 44 in the region of the tubular abutment wall 50. This large force is thereby applied directly through the relatively thick abutment wall 50 only to that portion of the plug and wickholder 16 which is directly above the bottle neck 18. In this way other portions of the cap 22 and of the plug and wickholder 16 are isolated from, and are not damaged by, this large assembly force.

The present invention enables the provision of maximum interference between the shoulder 24 of the bottle neck 18 and the bead 26 on the plug and wickholder skirt 36, without causing undue stresses that would otherwise affect the seal between the plug and wickholder 16 and the bottle neck 18 on the one hand and without affecting the seal between the cap 22 and the plug and wickholder 16 on the other hand.

Referring now to FIG. 1, the interference fit between the inner sealing wall 48 on the cap 22 and the inner and outer tubular walls 28 and 32 on the plug and wickholder 16 produces a finite amount of distortion in these walls. The consequential stresses produced by this distortion, however, is not communicated to the seal between the plug and wickholder 16 and the bottle neck 18. This is because the seal between the plug and wickholder 16 and the bottle neck 18 is provided by a separate, isolated element, namely, the cylindrical sealing wall 38. As a result, the plug and wickholder can be firmly secured to the bottle neck while secure and reliable seals are maintained between the cap and the plug and wickholder and between the plug and wickholder and the bottle.

Industrial Applicability

This invention improves the long term sealing of replaceable liquid reservoirs which contain liquids to be atomized in atomizer devices. It is possible to fill the reservoirs easily and to seal them reliably against leakage so that they can be stored for future use in an atomizer device. Further, this sealing is carried out without adversely affecting their unsealing when they are connected to an atomizing device.

What is claimed is:

1. A plug and wickholder comprising a unitary molded plastic piece which includes:

a first, generally vertical tubular wall for containing a wick a second, generally vertical tubular wall extending around and concentric with said first tubular wall, said first and second tubular walls being connected to each other near their lower ends thereof and tapering slightly away from each other in a direction toward their upper ends;

a generally horizontal upper wall which can be fitted over the top of a bottle neck, said upper wall being integral with and extending radially outwardly from said second tubular wall near its upper end;

a circumferential skirt extending down from the outer edge of said radially extending upper wall, said skirt being formed on its internal surface near the bottom edge thereof with at least one latch element to hold said skirt to the neck of a bottle; and a generally cylindrical sealing wall extending down from said upper wall between said skirt and said second tubular wall for fitting inside of and becoming sealed to the inside surface of a bottle neck when said at least one latch element holds said skirt to said bottle neck, said cylindrical wall being free of other structure at its lower edge.

2. A plug and wickholder according to claim 1, wherein at least one of the mutually facing surfaces of said first and second vertical tubular walls is tapered toward its upper end.

3. A plug and wickholder according to claim 1, wherein said generally cylindrical sealing wall is tapered toward its lower end.

4. A plug and wickholder according to claim 1, wherein said first and second generally vertical tubular walls are connected together near their lower ends via a lower radially extending wall.

5. A plug and wickholder according to claim 1, wherein the mutually facing surfaces of said first and second vertical tubular walls are sealing surfaces.

6. A combination comprising:

a plug and wickholder comprising a unitary molded plastic piece which includes:

a first, generally vertical tubular wall for containing a wick a second, generally vertical tubular wall extending around and parallel to said first tubular wall, said first and second tubular walls being connected to each other near their lower ends thereof;

a generally horizontal upper wall which can be fitted over the top of a bottle neck, said upper wall being integral with and extending radially outwardly from said second tubular wall near its upper end;

a circumferential skirt extending down from the outer edge of said radially extending upper wall, said skirt being formed on its internal surface near the bottom edge thereof with at least one latch element to hold said skirt to the neck of a bottle; and a generally cylindrical sealing wall extending down from said upper wall between said skirt and said second tubular wall for fitting inside of and becoming sealed to the inside surface of a bottle neck when said at least one latch element holds said skirt to said bottle neck, said cylindrical wall being free of other structure at its lower edge; and a sealing cap removably connected to said plug and wickholder, said sealing cap having a tubular cap sealing wall extending down from a top wall and sealingly fitted to the outer surface of said first generally vertical tubular wall.

7. A combination according to claim 6, wherein said cap sealing wall extends between and forms an interference fit with said first and second vertical tubular walls.

8. A combination according to claim 6, wherein at least one of the mutually facing surfaces of said first and second vertical tubular walls is tapered toward its upper end.

9. A combination according to claim 6, wherein said generally cylindrical sealing wall is tapered toward its lower end.

10. A combination according to claim 6, wherein said first and second generally vertical tubular walls are connected together near their lower ends via a lower radially extending wall.

11. A combination according to claim 6, wherein the mutually facing surfaces of said first and second vertical tubular walls form sealing surfaces with outer surfaces of said tubular cap sealing wall.

12. A combination comprising:

a plug and wickholder comprising a unitary molded plastic piece which includes:

a first, generally vertical tubular wall for containing a wick a second, generally vertical tubular wall extending around and parallel to said first tubular wall, said first and second tubular walls being connected to each other near their lower ends thereof a generally horizontal upper wall which can be fitted over the top of a bottle neck, said upper wall being integral with and extending radially outwardly from said second tubular wall near its upper end;

a circumferential skirt extending down from the outer edge of said radially extending upper wall, said skirt being formed on its internal surface near the bottom edge thereof with at least one latch element to hold said skirt to the neck of a bottle, and a generally cylindrical sealing wall extending down from said upper wall between said skirt and said second tubular wall for fitting inside of and becoming sealed to the inside surface of a bottle neck when said at least one latch element holds said skirt to said bottle neck, said cylindrical wall being free of other structure at its lower edge; and a bottle having a neck which fits between said circumferential skirt and said generally cylindrical sealing wall.

13. A combination according to claim 12, wherein said neck and said generally cylindrical sealing wall form an interference fit.

14. A combination according to claim 12, and further including a wick which extends from within said bottle and up through said first, generally vertical tubular wall.

15. A combination comprising:

a plug and wickholder comprising a unitary molded plastic piece which includes:

a first, generally vertical tubular wall for containing a wick a second, generally vertical tubular wall extending around and parallel to said first tubular wall, said first and second tubular walls being connected to each other near their lower ends thereof;

a generally horizontal upper wall which can be fitted over the top of a bottle neck, said upper wall being integral with and extending radially outwardly from said second tubular wall near its upper end;

a circumferential skirt extending down from the outer edge of said radially extending upper wall, said skirt being formed on its internal surface near the bottom edge thereof with at least one latch element to bold said skirt to the neck of a bottle; and a generally cylindrical sealing wall extending down from said upper wall between said skirt and said second tubular wall for fitting inside of and becoming sealed to the inside surface of a bottle neck when said at least one latch element holds said skirt to said bottle neck, said cylindrical wall being free of other structure at its lower edge;

a sealing cap removably connected to said plug and wickholder, said sealing cap having a tubular cap sealing wall extending down from a top wall and sealingly fitted to the outer surface of said first generally vertical tubular wall; and a bottle having a neck which fits between said circumferential skirt and said generally cylindrical sealing wall.

16. A combination according to claim 15, wherein at least one of the mutually facing surfaces of said first and second vertical tubular walls is tapered toward its upper end.

17. A combination according to claim 15, wherein said generally cylindrical sealing wall is tapered toward its lower end.

18. A combination according to claim 15, wherein said first and second generally vertical tubular walls are connected together near their lower ends via a lower radially extending wall.

19. A combination according to claim 15, wherein the mutually facing surfaces of said first and second vertical tubular walls are sealing surfaces.

20. A combination according to claim 15, wherein said cap sealing wall forms an interference fit with said first and second, generally vertical tubular walls.

21. A combination according to claim 15, wherein said neck and said generally cylindrical sealing wall form an interference fit.

22. A combination according to claim 15, and further including a wick which extends from within said bottle and up through said first, generally vertical tubular wall.

* * * * *